United States Patent [19]
Elmore

[11] Patent Number: 5,443,057
[45] Date of Patent: Aug. 22, 1995

[54] STERILIZABLE ENDOSCOPE AND METHOD FOR CONSTRUCTING THE SAME

[75] Inventor: J. Charles Elmore, Mission Viejo, Calif.

[73] Assignee: International Bioview, Inc., Irvine, Calif.

[21] Appl. No.: 135,895

[22] Filed: Oct. 12, 1993

[51] Int. Cl.6 ............................................. A61B 1/00
[52] U.S. Cl. ................................... 600/133; 600/182
[58] Field of Search ....................... 385/115, 117, 122; 128/4, 6, 7

[56] References Cited

U.S. PATENT DOCUMENTS

| | | | |
|---|---|---|---|
| 2,922,415 | 1/1960 | Campagna | 128/4 |
| 2,975,785 | 3/1961 | Sheldon | 128/6 |
| 3,144,020 | 8/1964 | Zingale | 128/4 |
| 3,162,190 | 12/1964 | Del Gizzo | 128/6 |
| 3,794,091 | 2/1974 | Ersek et al. | 150/52 R |
| 3,809,072 | 5/1974 | Ersek et al. | 128/23 |
| 3,866,601 | 2/1975 | Russell | 128/4 |
| 3,947,089 | 3/1976 | Rapp | 350/151 |
| 3,980,078 | 9/1976 | Tominaga et al. | 128/4 |
| 4,076,018 | 2/1978 | Heckele | 128/6 |
| 4,085,742 | 4/1978 | Okada | 128/4 |
| 4,132,227 | 1/1979 | Ibe | 128/4 |
| 4,201,199 | 5/1980 | Smith | 128/7 |
| 4,248,214 | 2/1981 | Hannah et al. | 128/7 |
| 4,254,762 | 3/1981 | Yoon | 128/4 |
| 4,327,735 | 5/1982 | Hampson | 128/348 |
| 4,329,995 | 5/1982 | Anthracite | 128/350 R |
| 4,624,243 | 11/1986 | Lowery et al. | 128/6 |
| 4,646,722 | 3/1987 | Silverstein | 128/4 |
| 4,757,381 | 7/1988 | Cooper et al. | 358/98 |
| 4,770,653 | 9/1988 | Shturman | 604/21 |
| 4,776,340 | 10/1988 | Moran et al. | 128/634 |
| 4,813,400 | 3/1989 | Washizuka et al. | 128/6 |
| 4,854,302 | 8/1989 | Allred, III | 128/6 |
| 4,858,001 | 8/1989 | Milbank et al. | 128/6 X |
| 4,869,238 | 9/1989 | Opie et al. | 128/6 |
| 4,916,534 | 4/1990 | Takahashi et al. | 358/98 |
| 5,235,283 | 8/1993 | Lehne | 128/653.5 X |
| 5,335,647 | 8/1994 | Brustad | 128/4 |
| 5,347,990 | 9/1994 | Ebling et al. | 128/4 |

FOREIGN PATENT DOCUMENTS 1405025  9/1975  United Kingdom .

OTHER PUBLICATIONS

Olympus Optical Co., Ltd., Instruction Manual for the Olympus of Type PIOS, OES Sigmoidofiberscope, p. 17.

Designer's Handbook: Medical Electronics, "Hybrid Cables Reduce Clutter and Failures", pp. 10–11.

Fiber Optics Handbook For Engineers and Scientists, Chapter 2, "Fiber-Optic Cables", by M. M. Ramsay, 12 pages.

Collimated Holes, Inc., "Flexible Fiber Bundles and Light Guide Material", 2 pages.

*Primary Examiner*—Richard J. Apley
*Assistant Examiner*—Beverly M. Flanagan
*Attorney, Agent, or Firm*—Stetina Brunda & Buyan

[57] ABSTRACT

A gas sterilizable endoscope has a cannula having proximal and distal ends and a fiber optic imaging bundle disposed within the cannula. A first attachment, e.g., a first thermally curable epoxy bond, is formed at the proximal end of the cannula so as to attach the fiber optic imaging bundle to the cannula at the proximal end thereof. A second attachment, e.g., a second thermally curable epoxy bond, is formed at the distal end of the cannula so as to similarly attach the fiber optic imaging bundle to the cannula at the distal end thereof. A bow is formed in the fiber optic imaging bundle such that tensile stress formation in the fiber optic imaging bundle resulting from thermal expansion of the cannula during gas sterilization is mitigated.

17 Claims, 2 Drawing Sheets

STERILIZABLE ENDOSCOPE AND METHOD FOR CONSTRUCTING THE SAME

FIELD OF THE INVENTION

The present invention relates generally to medical devices and more particularly to a gas sterilizable endoscope wherein a bow is formed in the fiber optic imaging bundle so as to mitigate tensile stress formation in the fiber optic imaging bundle during gas sterilization.

BACKGROUND OF THE INVENTION

The use of endoscopes for diagnostic and therapeutic purposes is well known in the medical arts. Various types of endoscopes are available for various particular applications. For example, upper endoscopes are utilized for the examination of the esophagus, stomach, and duodenum; colonoscopes are utilized for the examination of the colon; angioscopes are utilized for the examination of various blood vessels; brochioscopes are utilized for examination of the bronchi; laparoscopes are utilized for examination of the peritoneal cavity; and arthroscopes are utilized for the examination of various joint spaces. Examples of such endoscopes are provided in U.S. Pat. Nos. 2,922,415; 3,162,190; 4,076,018; 4,132,227; 4,201,199; 4,254,762; and 4,916,534.

Rigid endoscopes are typically used in laparoscopic procedures wherein the endoscope is inserted into a body cavity, e.g., a pneumoperitoneum, through a trocar. The use of endoscopes in such procedures minimizes trauma to the patient and also minimizes the expense associated with the procedure.

Although endoscopes provides tremendous advantages in the diagnosis and treatment therapy of many medical conditions, contemporary endoscopes are limited in their capability for repeated use. One problem commonly associated with such endoscopes is that of sterilization. Sterilization is necessary in order to facilitate reuse of the endoscope. In order to prevent the transmission of various pathogens, it is necessary to sterilize endoscopes between uses. This is of particular concern in contemporary times because of the threat of such viral infections as HIV and hepatitis A.

Although it is known to sterilize endoscopes with heat or chemical agents, the preferred method of sterilization is gas sterilization. In such gas sterilization process, the endoscope is subjected to a sterilizing gas introduced into a sterilizing chamber typically maintained at a temperature of approximately 45°-55° C. Contemporary endoscopes are particularly susceptible to heat damage occasioned during such gas sterilization.

In this regard, it is common for contemporary endoscopes to experience damage to the fiber optic imaging bundle disposed therein when subjected to the elevated temperatures associated with gas sterilization. Contemporary sterilization protocol requires that endoscopes be heated to approximately 45°-55° C. This is sufficient to cause the elongate cannula within which the fiber optic imaging bundle is disposed to thermally expand, i.e., increase in length, so as to stretch the enclosed fiber optic imaging bundle to the point where the stress within the fiber optic imaging bundle generated by such stretching causes the fiber optic imaging bundle to crack, break, or otherwise degrade.

As such, it would be beneficial to provide an endoscope which is capable of tolerating the elevated temperatures involved in gas sterilization without experiencing breakage or other degradation thereof.

SUMMARY OF THE INVENTION

The present invention specifically addresses and alleviates the above-mentioned deficiencies associated with the prior art. More particularly, the present invention comprises a gas sterilizable endoscope comprising a cannula having proximal and distal ends and a fiber optic imaging bundle disposed within the cannula. A first attachment, e.g., a first thermally curable epoxy bond, is formed at the proximal end of the cannula so as to attach the fiber optic imaging bundle to the cannula at the proximal end thereof. A second attachment, e.g., a second thermally curable epoxy bond, is formed at the distal end of the cannula so as to similarly attach the fiber optic imaging bundle to the cannula at the distal end thereof. A bow is formed in the fiber optic imaging bundle such that tensile stress formation in the fiber optic imaging bundle resulting from thermal expansion of the cannula during heat sterilization is mitigated for heat sterilization at temperatures of up to approximately 45°-60° C.

The cannula preferably comprises a portion of increased inner diameter formed proximate the proximal end thereof and optimally is formed of a polymer material having a thermal coefficient of expansion approximating that of the remainder, i.e., the elongate portion of the cannula. The portion of increased inner diameter is preferably comprised of ABS, although those skilled in the art will recognize that various other materials are likewise suitable.

The endoscope is preferably constructed by inserting a fiber optic imaging bundle into a cannula and then attaching one end of the cannula, preferably the distal end thereof, to the fiber optic imaging bundle. The cannula is then heated so as to effect thermal expansion, i.e., increase in the length, of the cannula and thereby equilibrate the temperature of both the image bundle and cannula. Next, the other end of the cannula is attached to the fiber optic imaging bundle. The cannula is then cooled.

As the cannula cools, a bow forms in the fiber optic imaging bundle due to the difference in the thermal coefficients of expansion of the cannula and the fiber optic imaging bundle. Such fiber optic imaging bundles are typically comprised of glass or quartz and such cannulae are typically comprised of a metal such as stainless steel. Thus, as those skilled in the art will recognize, the cannula of such endoscopes has a substantially higher thermal coefficient of expansion than the fiber optic imaging bundle thereof. The cannula therefore expands more during heating thereof and also contracts more during cooling thereof.

The bow formed in the fiber optic imaging bundle mitigates tensile stress formation in the fiber optic imaging bundle during subsequent gas sterilization. During subsequent gas sterilization the cannula once again expands, thus straightening the bow formed in the fiber optic imaging bundle. The cannula is heated to a temperature equal to or in excess of that experienced during gas sterilization such that the bow does not pull taut during gas sterilization, thus substantially limiting the amount of tension applied to the fiber optic imaging bundle during gas sterilization. As such, the bow facilitates thermal expansion and more particularly the difference in thermal expansion between the cannula and image bundle.

The proximal and distal ends of the cannula are preferably attached to the fiber optic imaging bundle via a thermally curable epoxy. Thus, prior to heating the cannula so as to effect thermal expansion thereof, one end, preferably the distal end, of the cannula is bonded to the fiber optic imaging bundle via such thermally curable epoxy and the epoxy is then heat cured. Next, thermally curable adhesive is applied to the proximal end of the cannula so as to bond the fiber optic imaging bundle thereto upon curing. The cannula is then heated to a temperature of approximately 65° C. so as to both effect thermal expansion, i.e., increase in length, of the cannula and to cure the thermally curable epoxy formed at the proximal end of the cannula. After the thermally curable epoxy at the proximal end of the cannula is thus cured, the cannula is cooled to room temperature.

These, as well as other, advantages of the present invention will be more apparent from the following description and drawings. It is understood that changes in the specific structure shown and described may be made within the scope of the claims without departing from the spirit of the invention.

DETAILED DESCRIPTION OF THE PREFERRED EMBODIMENT

The detail description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 1:
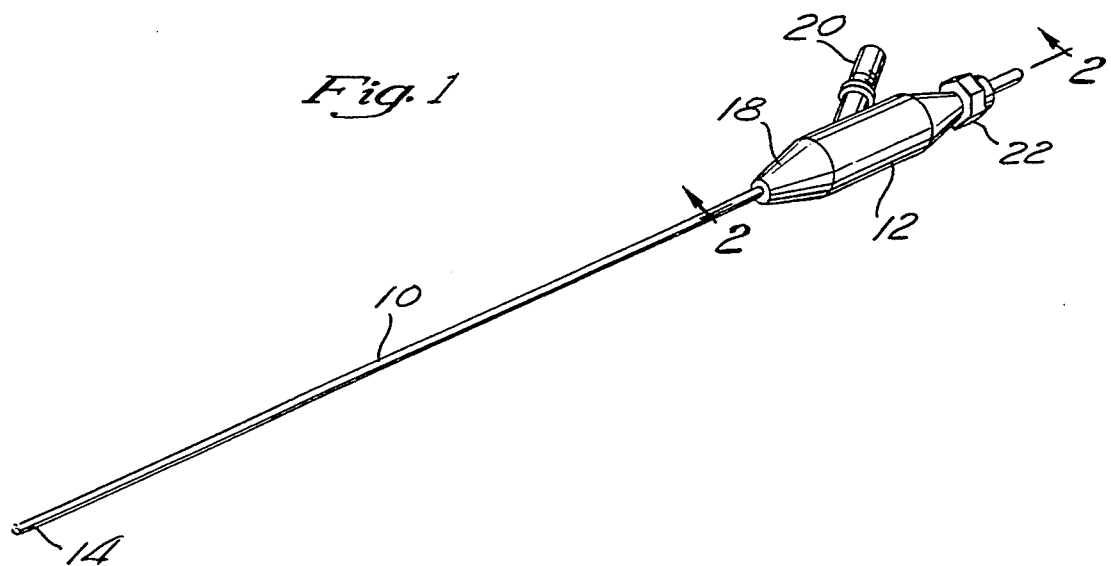
FIG. 1 is a perspective view of the gas sterilizable endoscope of the present invention.
Figure 2:
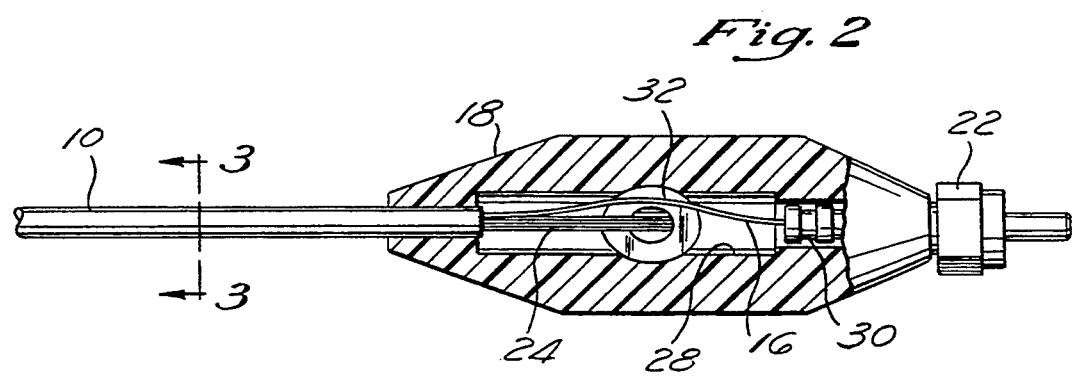
FIG. 2 is an enlarged view, partly in cross-section, of the proximal end of the gas sterilizable endoscope of FIG. 1.
Figure 3:
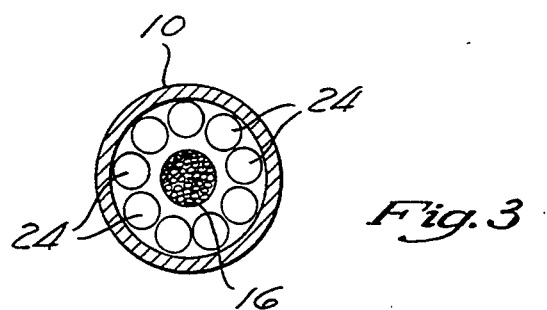
FIG. 3 is a cross-sectional view taken along lines 3 of FIG. 2.
Figure 4:
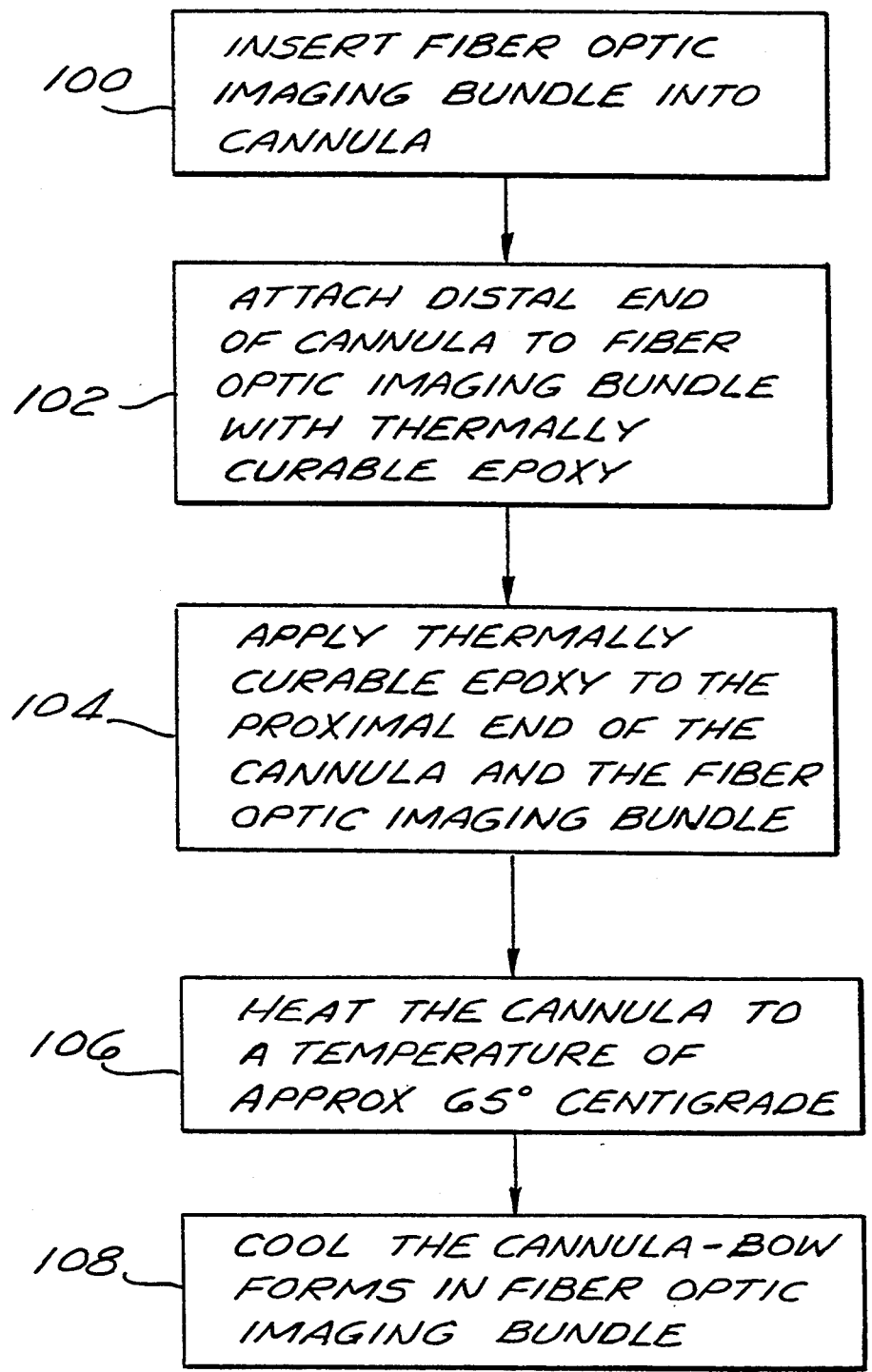
FIG. 4 is a flow chart illustrating the steps of constructing a gas sterilizable endoscope according to the method of the present invention.

The sterilizable endoscope of the present invention is illustrated in FIGS. 1-3 which depict a presently preferred embodiment of the invention and the method for constructing the same is illustrated in FIG. 4. Referring now to FIGS. 1-3, the sterilizable endoscope is comprised generally of a cannula 10 having proximal 12 and distal 14 ends. A conventional fiber optic imaging bundle 16 (shown in FIGS. 2 and 3) is disposed within the cannula and extends generally from the proximal end 12 to the distal end 14 thereof.

The fiber optic imaging bundle 16 is attached to the proximal and distal ends of the cannula.

A portion of increased inner diameter 18 is preferably formed proximate the proximal end 12 of the cannula 10. The portion of increased inner diameter preferably defines a Y-junction having an illumination connector 20 branching off at an angle therefrom and having an eyepiece connector 22 formed in line with the cannula 10. Those skilled in the art will recognize that various other configurations of the illumination connector 20 and the eyepiece connector 22 are likewise suitable.

The portion of increased inner diameter 18 is preferably comprised of a polymer material such as ABS. The portion of increased inner diameter optimally comprises a material having a thermal coefficient of expansion approximating that of the remainder of the cannula 10, however oftentimes is formed of a material that has a greater thermal coefficient of expansion such that greater expansion occurs within the portion of increased inner diameter 18 than occurs within the remainder of the cannula 10 during heating thereof.

As those skilled in the art will appreciate, in use, the distal end 14 of the cannula 10 is inserted through a trocar (not shown) during laparoscopic procedures. A source of illumination is attached to the illumination connector 20 and an eyepiece, preferably adapted for a video camera, is attached to the eyepiece connector 22.

With particular reference to FIG. 2, the sterilizable endoscope of the present invention further comprises a plurality of illumination fibers 24 which extend along with the optical imaging bundle 16 substantially along the length of the cannula 10. The illumination fibers 24 extend through opening 26 formed in the portion of increased inner diameter 18 and out through the illumination connector 20 to facilitate attachment to a source of illumination. The optical imaging bundle 16 passes through the enlarged bore 28 of the portion of increased inner diameter 18 and out through the proximal end portion 30 of the cannula 10 to the eyepiece connector 22. A bow 32 is formed in the optical imaging bundle 16, preferably within the bore 28, when the gas sterilizable endoscope of the present invention is not heated, i.e., is at approximately ambient temperature.

With particular reference to FIG. 3, the optical imaging bundle 16 is preferably surrounded by a plurality of individual illumination fibers 24 which extend along therewith to the distal end of the cannula 10 so as to provide illumination.

As those skilled in the art will recognize, the optical imaging bundle 16 comprises a plurality, approximately 6,000 for example, of individual optical fibers so as to facilitate imaging. The individual optical fibers of the optical imaging bundle 16 preferably comprise quartz. The illumination fibers 24 may comprise quartz, glass, or a polymer material.

The cannula 10 is preferably formed of stainless steel, such that it is biologically compatible and is suitable for gas sterilization. Those skilled in the art will recognize that the stainless steel cannula has a greater thermal coefficient of expansion than either the fiber optic imaging bundle 16 or the illumination fibers 24. Thus, upon moderate heating of the sterilizable endoscope of the present invention, as in gas sterilization thereof, the cannula 10 expands, i.e., increases in length, substantially more than the illumination fibers 24 or the optical imaging bundle 16.

As those skilled in the art will recognize, such expansion of the cannula in contemporary devices, i.e., during the gas sterilization process, typically results in damage to the delicate optical imaging bundle, as tension is applied thereto. Such tension results from the attachment of the optical imaging bundle at the proximal and distal ends of the cannula. Such attachment results in pulling of the optical imaging bundle as the length of the cannula increases, thus applying tension to the optical imaging bundle and frequently cracking, breaking, or otherwise damaging the individual fibers thereof. As such, contemporary endoscopes are not suitable for heat sterilization.

According to the method for constructing the sterilizable endoscope of the present invention, the fiber optic imaging bundle 16 is inserted within the cannula 10. Either the proximal 12 or the distal 14 end of the cannula is then attached to the fiber optic imaging bundle 16. Next, the cannula is heated to a temperature equal to or in excess of that experienced during gas sterilization, i.e., preferably to approximately 65° C. At this elevated temperature wherein both the cannula and image bundle are at the same temperature, the other end of the cannula is then attached to the fiber optic imaging bundle 16. Optionally, the illumination fibers 24 may be attached or bonded to the cannula 10 contemporaneously with the optical imaging bundle 16. Next, the cannula is cooled to ambient temperature.

By this mounting procedure, a bow 32 is formed in the fiber optic imaging bundle, preferably within the portion of increased inner diameter 18 upon cooling of the cannula 10. The bow 32 mitigates tensile stress formation in the fiber optic imaging bundle 16 by accommodating thermal expansion occurring during the moderate heating associated with subsequent gas sterilization.

The step of attaching one end of the cannula 10 to the fiber optic imaging bundle 16 preferably comprises epoxying, preferably via a thermally curable epoxy, as does the step of attaching the opposite end of the cannula 10 to the fiber optic imaging bundle 16.

The distal end of the cannula 10 is preferably epoxied to the fiber optic imaging bundle 16 prior to heating of the cannula 10.

Referring now to FIG. 4, the method for constructing a gas sterilizable endoscope according to the present invention more particularly comprises the steps of: inserting the fiber optic imaging bundle into the cannula 100; attaching the distal end of the cannula to the fiber optic imaging bundle with thermally curable epoxy 102; applying a thermally curable epoxy to the proximal end of the cannula 104; heating the cannula to a temperature of approximately 65° C. 106; and cooling the cannula 108.

Optionally, the illumination fibers 24 may contemporaneously be inserted into the cannula 10 along with the fiber optic imaging bundle 16. Optionally, the distal end of the cannula 10 may contemporaneously be attached to the illumination fibers 24 along with the bundle 16. Optionally, the thermally curable epoxy may contemporaneously be applied to the illumination fibers 24 along with the fiber optic imaging bundle 16.

The step 102 of attaching the distal end of the cannula to the fiber optic imaging bundle with thermally curable epoxy 102 comprises applying the thermally curable epoxy to the distal end 14 of the cannula 10 and the fiber optic imaging bundle 16 and then thermally curing the epoxy so as to effect attachment. The step 104 of applying a thermally curable epoxy to the proximal end of the cannula 104 comprises merely applying the thermally curable epoxy to the proximal end of the cannula as well as to the fiber optic imaging bundle 16.

The step 106 of heating the cannula 10 to a temperature of approximately 65° C. preferably comprises placing the cannula 10, having the fiber optic imaging bundle 16 therein, into a thermostatically controlled heater. It will be appreciated that both the cannula 10 and the fiber optic imaging bundle 16 are heated simultaneously such that both the cannula and imaging bundle equilibrate in temperature at 65° C. prior to bonding together via the thermally curing epoxy. Those skilled in the art will recognize that various other means for heating the cannula 10 are likewise suitable. For example, the cannula 10 may be heated via electrical heating elements, the application of heated air, etc.

The step 108 of cooling the cannula 10 preferably comprises air cooling the cannula 10 merely by discontinuing application of heat. The cannula 10 may alternatively be cooled by blowing ambient air thereover. Those skilled in the art will recognize that various means for cooling the cannula 10 are likewise suitable.

Upon cooling a bow 32 forms within the bore 28 of the portion of increased inner diameter 18 so as to mitigate the formation of tensile stress in the fiber optic imaging bundle during subsequent gas sterilization wherein the cannula is heated to a temperature less than 65° C., preferably between 45°–50° C.

At such gas sterilization temperatures, the cannula 10 expands, i.e., increases in length, by an amount substantially less than that which occurred during construction of the gas sterilizable endoscope of the present invention, thus eliminating substantial tension upon the fiber optic imaging bundle 32 thereof.

It will be understood that the exemplary sterilizable endoscope described herein and shown in the drawings represents only a presently preferred embodiment of the invention. Indeed, various modifications and additions may be made to such embodiment without departing from the spirit and scope of the invention. For example, various lumens may be provided within the cannula 10 to facilitate the introduction of various medications and/or medical devices, i.e., guidewires, balloon catheters, etc. Also, it will be appreciated that the cannula may alternatively be heated to a temperature other than 65° C. during the fabrication process so as to accommodate sterilization at different temperatures. It is only necessary that the cannula be heated to a temperature generally commensurate to that utilized during sterilization. Also, it will be appreciated that the apparatus and method of the present invention need not be limited to rigid endoscopes utilized in laparoscopic procedures, but rather may extend to various different types of endoscopes utilized in various procedures. Thus, these and other modifications and additions may be obvious to those skilled in the art and may be implemented to adapt the present invention for use in a variety of different applications.

What is claimed is:

1. A gas sterilizable endoscope comprising:
   a) a rigid cannula having proximal and distal ends;
   b) a fiber optic imaging bundle disposed within said cannula;
   c) said fiber optic imaging bundle being attached to the proximal and distal ends of said cannula; and
   d) a bow formed in said fiber optic imaging bundle such that tensile stress formation in the fiber optic imaging bundle is mitigated during heat sterilization.

2. The endoscope as recited in claim 1 wherein said first and second attachments comprise epoxy.

3. The endoscope as recited in claim 1 wherein said first and second attachments comprise thermally curable epoxy.

4. The endoscope as recited in claim 1 wherein the bow formed in said fiber optic imaging bundle mitigates tensile stress formation in the fiber optic imaging bundle during heat sterilization up to a temperature of approximately 65° C.

5. The endoscope as recited in claim 1 wherein said cannula further comprises a portion of increased inner diameter formed proximate the proximal end thereof, said bow being formed within said portion of increased diameter.

6. The endoscope as recited in claim 5 wherein said portion of increased inner diameter is comprised of a polymer material.

7. The endoscope as recited in claim 5 wherein said portion of increased inner diameter is formed of ABS.

8. The endoscope as recited in claim 5 wherein said portion of increased inner diameter comprises a material having a greater thermal coefficient of expansion than that of the remainder of the cannula.

9. A gas sterilizable endoscope comprising:
 a) a rigid cannula having proximal and distal ends and having a portion of increased inner diameter formed proximate the proximal end thereof;
 b) a fiber optic imaging bundle disposed within said cannula;
 c) a first thermally curable epoxy bond formed at the proximal end of the cannula attaching said fiber optic imaging bundle to the cannula;
 d) a second thermally curable epoxy bond formed at the distal end of the cannula attaching said fiber optic imaging bundle to the cannula; and
 e) a bow formed in said fiber optic imaging bundle in the portion of increased inner diameter of said cannula such that tensile stress formation in the fiber optic imaging bundle is mitigated during gas sterilization.

10. A gas sterilizable endoscope comprising:
 a) a rigid cannula having proximal and distal ends, said cannula comprising a portion of increased inner diameter formed proximate the proximal end thereof, the portion of increased diameter comprising a material having a greater thermal coefficient of expansion than that of the remainder of the cannula;
 b) a fiber optic imaging bundle disposed within said cannula;
 c) a first attachment formed at the proximal end of the cannula attaching the fiber optic imaging bundle to the cannula;
 d) a second attachment formed at the distal end of the cannula attaching the fiber optic imaging bundle to the cannula; and
 e) a bow formed in said fiber optic imaging bundle within the portion of increased diameter of said cannula such that tensile stress formation in the fiber optic imaging bundle is mitigated during heat sterilization.

11. The endoscope as recited in claim 10 wherein said first and second attachments comprise epoxy.

12. The endoscope as recited in claim 10 wherein said first and second attachments comprise thermally curable epoxy.

13. The endoscope as recited in claim 10 wherein the bow formed in said fiber optic imaging bundle mitigates tensile stress formation in the fiber optic imaging bundle during heat sterilization up to a temperature of approximately 65° C.

14. The endoscope as recited in claim 10 wherein said cannula further comprises a portion of increased inner diameter formed proximate the proximal end thereof, said bow being formed within said portion of increased diameter.

15. The endoscope as recited in claim 14 wherein said portion of increased inner diameter is comprised of a polymer material.

16. The endoscope as recited in claim 14 wherein said portion of increased inner diameter is formed of ABS.

17. A gas sterilizable endoscope comprising:
 a) a rigid cannula having proximal and distal ends and having a portion of increased inner diameter formed proximate the proximal end thereof, said portion of increased inner diameter comprising a material having a greater thermal coefficient of expansion than the remainder of the cannula;
 b) a fiber optic imaging bundle disposed with said cannula;
 c) a first thermally curable epoxy bond formed at the proximal end of the cannula attaching said fiber optic imaging bundle to the cannula;
 d) a second thermally curable epoxy bond formed at the distal end of the cannula attaching said fiber optic imaging bundle to the cannula; and
 e) a bow formed in said fiber optic imaging bundle in the portion of increased inner diameter of said cannula such that tensile stress formation in the fiber optic imaging bundle is mitigated during gas sterilization.

* * * * *